United States Patent [19]

Murdock

[11] 4,428,882

[45] Jan. 31, 1984

[54] 1-(AMINOALKYLAMINO)-5,8-DIHYDROXY-4-SUBSTITUTED-ANTHRAQUINONES

[75] Inventor: Keith C. Murdock, Pearl River, N.Y.

[73] Assignee: American Cyanamid Company, Stamford, Conn.

[21] Appl. No.: 351,804

[22] Filed: Feb. 24, 1982

Related U.S. Application Data

[60] Continuation-in-part of Ser. No. 258,986, Apr. 24, 1981, abandoned, which is a division of Ser. No. 43,271, May 29, 1979, Pat. No. 4,275,009.

[51] Int. Cl.³ .............................................. C07C 97/26
[52] U.S. Cl. ...................................... 260/379; 260/380
[58] Field of Search ........................ 260/378, 379, 380

[56] References Cited

U.S. PATENT DOCUMENTS 3,123,605  3/1964  Turetzky et al. .................... 260/380
4,138,415  2/1979  Murdock et al. .................... 260/380

*Primary Examiner*—Natalie Trousof
*Assistant Examiner*—Raymond K. Covington
*Attorney, Agent, or Firm*—Edward A. Conroy, Jr.

[57] ABSTRACT

This disclosure describes 1-(aminoalkylamino)-5,8-dihydroxy-4-substituted-anthraquinones useful as chelating agents and for inhibiting the growth of transplanted mouse tumors.

3 Claims, No Drawings

1-(AMINOALKYLAMINO)-5,8-DIHYDROXY-4-SUBSTITUTED-ANTHRAQUINONES

CROSS REFERENCE TO RELATED APPLICATION

This application is a continuation-in-part of my co-pending application Ser. No. 258,986, filed Apr. 24, 1981, which is a division of my application Ser. No. 43,271, filed May 29, 1979, now U.S. Pat. No. 4,275,009.

BRIEF SUMMARY OF THE INVENTION

This invention relates to new organic compounds and, more particularly, is concerned with novel 1-(aminoalkylamino)-5,8-dihydroxy-4-substituted-anthraquinones which may be represented by the following general formula:

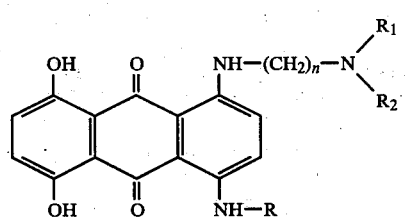
(I)

wherein n is an integer from 2 to 4, inclusive; R is hydrogen or alkyl having from one to three carbon atoms; and $R_1$ and $R_2$ are each individually selected from the group consisting of hydrogen, alkyl having from 1 to 3 carbon atoms and monohydroxyalkyl having from 2 to 4 carbon atoms and wherein the carbon atom alpha to the nitrogen atom may not bear an hydroxy group.

A preferred embodiment of the present invention comprises certain 1-(aminoalkylamino)-4-amino-5,8-dihydroxyanthraquinones may be represented by the following general formula:

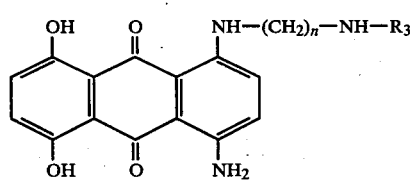

wherein n is an integer from 2 to 4, inclusive, and $R_3$ is monohydroxyalkyl as hereinabove defined.

Also included within the purview of the present invention are the leuco bases and tautomers thereof which may be represented by the following general formulae:

(II, leuco bases)

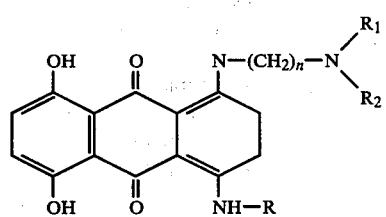

(III, tautomeric bases)

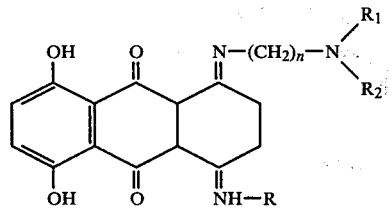

wherein n, R, $R_1$ and $R_2$ are as hereinabove defined.

DETAILED DESCRIPTION OF THE INVENTION

The novel compounds of the present invention are obtainable as reddish brown to blue crystalline materials having characteristic melting points and absorption spectra and which may be purified by leaching with lower alkanols since many of the free bases are insoluble in water and some of them are insoluble in most organic solvents. The organic bases of this invention (I, II, and III) form nontoxic acid-addition salts with a variety of pharmacologically acceptable organic and inorganic salt-forming reagents. Thus, acid-addition salts, formed by admixture of the organic free base with an acid, suitably in a neutral solvent, are formed with such acids as sulfuric, phosphoric, hydrochloric, hydrobromic, sulfamic, citric, lactic, malic, succinic, tartaric, acetic, benzoic, gluconic, ascorbic, and the like. For purposes of this invention the free bases are equivalent to their non-toxic acid-addition salts. The acid-addition salts of the organic bases of the present invention are, in general, crystalline solids, relatively soluble in water, methanol and ethanol but relatively insoluble in non-polar organic solvents such as diethyl ether, benzene, toluene, and the like.

The novel compounds of the present invention may be readily prepared in accordance with the following reaction scheme:

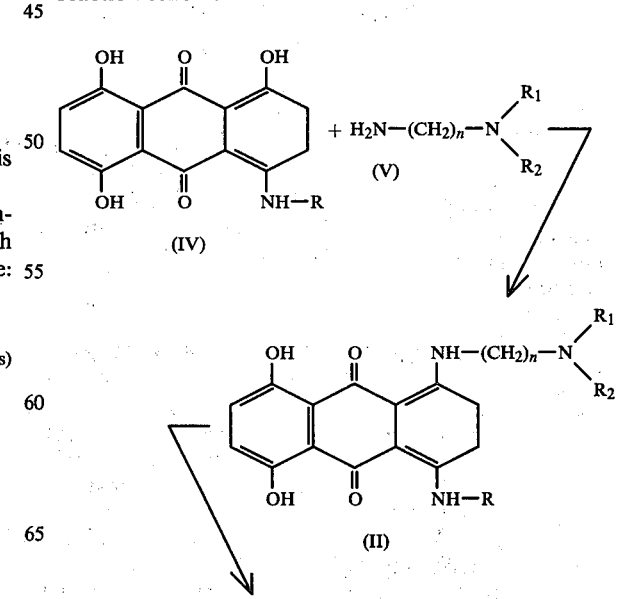

-continued

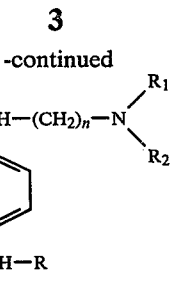

(I)

wherein n, R, $R_1$ and $R_2$ are as hereinabove defined. In accordance with this reaction scheme, leuco 1-(amino or alkylamino)-4,5,8-trihydroxyanthraquinone (IV) is condensed with an appropriate alkylene diamine (V) in a solvent such as N,N,N',N'-tetramethylethylenediamine, methanol, ethanol, water, dimethylformamide, or mixtures thereof at from about 40° C. to about 60° C. under an atmosphere of nitrogen for several hours to produce the corresponding leuco bases (II). The leuco bases (II) may be readily oxidized to the fully aromatic derivatives (I) by a variety of methods such as air oxidation or treatment with hot nitrobenzene, or treatment with chloranil, hydrogen peroxide or sodium perborate.

Alternatively the novel compounds of the present invention may be prepared in accordance with the following reaction scheme:

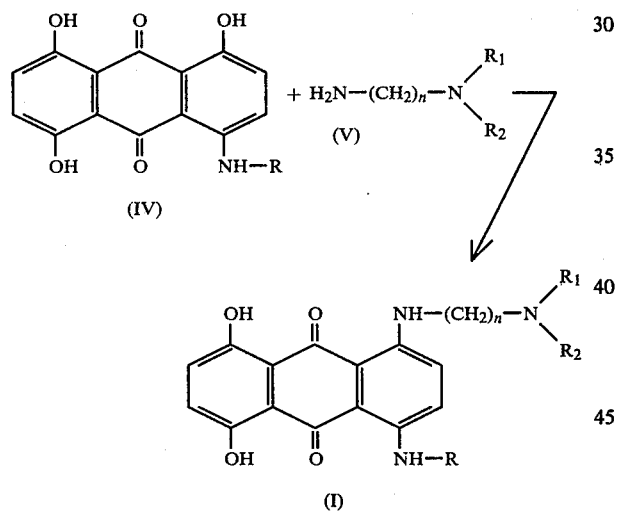

wherein n, R, $R_1$ and $R_2$ are as hereinabove defined. In accordance with this reaction scheme, 1-(amino or alkylamino)-4,5,8-trihydroxy-9,10-anthracenedione (VI) is condensed with an appropriate alkylene diamine (V) in a solvent such as N,N,N',N'-tetramethylethylenediamine, 2-methoxyethanol, or N,N-dimethylformamide and the like at the reflux temperature for 1–20 hours to produce the corresponding bases.

The novel compounds described herein are useful as chelating, complexing or sequestering agents. The complexes formed with polyvalent metal ions are particularly stable and usually soluble in various organic solvents. These properties, of course, render them useful for a variety of purposes wherein metal ion contamination presents a problem; e.g., as stabilizers in various organic systems such as saturated and unsaturated lubricating oils and hydrocarbons, fatty acids and waxes, wherein transition metal ion contamination accelerates oxidative deterioration and color formation. They are further useful in analyses of polyvalent metal ions which may be complexed or extracted by these materials and as metal carriers. Other uses common to sequestering agents are also apparent for these compounds. In addition, the leuco bases (II) are useful as intermediates in the preparation of the fully aromatic derivatives (I).

The novel compounds of the present invention also possess the property of inhibiting the growth of transplanted mouse tumors as established by the following tests.

LYMPHOCYTIC LEUKEMIA P388 TEST

The animals used as DBA/2 mice all of one sex, weighing a minimum of 17 g. and all within a 3 gram weight range. There are 5 or 6 animals per test group. The tumor transplant is by intraperitoneal injection of 0.1 ml. of dilute ascitic fluid containing $10^6$ cells of lymphocytic leukemia P388. The test compounds are administered intraperitoneally on days one, 5 and 9 (relative to tumor inoculation) at various doses. The animals are weighed and survivors are recorded on a regular basis for 30 days. The median survival time and the ratio of survival time for treated (T)/control (C) animals are calculated. The positive control compound is 5-fluorouracil given as a 60 mg./kg. injection. The results of this test with representative compounds of the present invention appear in Table I. The criterion for efficacy is $T/C \times 100 \geq 125\%$.

TABLE I

| | Lymphocytic Leukemia P388 Test | | |
|---|---|---|---|
| Compound | Dose (mg./kg.) | Median Survival Time (Days) | T/C × 100 (Percent) |
| 1-[2-(2-Hydroxyethylamino)-ethylamino]-4-amino-5,8-dihydroxyanthraquinone | 6 | 25 | 203 |
| | 3 | 22 | 179 |
| Control | 0 | 12.3 | — |
| 5-Fluorouracil | 60 | 15.0 | 150 |
| 1-[(3-Dimethylamino)propyl)-amino]-4-ethylamino-5,8-dihydroxyanthraquinone | 100 | 15 | 150 |
| | 50 | 14 | 140 |
| | 25 | 13 | 130 |
| Control | 0 | 10 | — |
| 5-Fluorouracil | 20 | 16 | 160 |

Also embraced within the purview of the present invention are therapeutic compositions of matter useful for ameliorating cancer diseases in mammals and containing the novel 9,10-anthracenediones (I) of the present invention (or the leuco bases and non-toxic acid-addition salts thereof). This aspect of the invention includes the novel compositions of matter and the method of inducing the regression and/or palliation of leukemia and related cancers in mammals therewith.

The active ingredients of the therapeutic compositions of the present invention inhibit transplanted mouse tumor growth and induce regression and/or palliation of leukemia and related cancers in mammals when administered in amounts ranging from about 1 mg. to about 0.4 g. per kilogram of body weight per day. A preferred dosage regimen for optimum results would be from about 1.0 mg. to about 50 mg. per kilogram of body weight per day, and such dosage units are employed that a total of from about 70 mg. to about 3.5 g.

of the active compound for a subject of about 70 kg. of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. A decided practical advantage is that the active compound may be administered in any convenient manner such as by the oral, intravenous, intramuscular, or subcutaneous routes.

The active compounds may be orally administered, for example, with an inert diluent or with an assimilable edible carrier, or they may be enclosed in hard or soft shell gelatin capsules, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations, may, of course, be varied and may conveniently be between about 2 to about 60% of the weight of the unit. The amount of active compound in such therapeutically useful compositions is such that a suitable dosage will be obtained. Preferred compositions or preparations according to the present invention are prepared so that an oral dosage unit form contains between about 1 and 400 milligrams of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compounds may be incorporated into sustained-release preparations and formulations.

The active compounds may also be administered parenterally or intraperitoneally. Solutions of the active compound as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases it will be preferable to include isotonic agents, for example sugars or sodium chloride. Prolonged absorption of the injectable compositions can be brought about by the use in the compositions of agents delaying absorption, for example aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatable with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically-acceptable carrier in dosage unit form as hereinbefore disclosed. A unit dosage form can, for example, contain the principal active compound in amounts ranging from about 0.1 to about 500 mg., with from about 10 to about 500 mg. being preferred. Expressed in proportions, the active compound is generally present in from about 10 to about 500 mg./ml. of carrier. In the case of compositions containing supplementary active ingredients, the dosages are determined by reference to the usual dose and manner of administration of the said ingredients.

Regression and palliation of cancers are attained, for example, using intraperitoneal administration. A single intravenous dosage or repeated daily dosages can be administered. Daily dosages up to about 5 or 10 days are often sufficient. It is also possible to dispense one daily dosage or one dose on alternate or less frequent days. As can be seen from the dosage regimens, the amount of principal active ingredient administered is a sufficient amount to aid regression and palliation of the leukemia or the like, in the absence of excessive deleterious side effects of a cytotoxic nature to the hosts harboring the cancer. As used herein, cancer disease means blood malignancies such as leukemia, as well as other solid and non-solid malignancies such as the melanocarcinomas, lung carcinomas, and mammary tumors. By regression and palliation is meant arresting or retarding the growth of the tumor or other manifestation of the disease compared to the course of the disease in the absence of treatment.

This invention will be described in greater detail in conjunction with the following specific examples.

EXAMPLE 1

1-[(3-Dimethylaminopropyl)amino]-4-ethylamino-5,8-dihydroxyanthraquinone

A mixture of 2.74 g. of leuco-1,4,5,8-tetrahydroxyanthraquinone, 0.45 g. of ethylamine, a trace of sodium hydrosulfite and 60 ml. of aqueous methanol was stirred and warmed to 50° C. for one hour. To this was added 1.1 g. of dimethylaminopropylamine and the mixture was stirred and warmed at 50°-60° C. for 2 hours. Air was bubbled through this mixture while heating on a steambath for 6 hours. The mixture was cooled and the title product was collected.

EXAMPLE 2

1-[2-(2-Hydroxyethylamino)ethylamino]-4-amino-5,8-dihydroxyanthraquinone monoformate A 260 ml. amount of 2-methoxyethanol in a 500 ml. round bottomed flask was stirred with a magnetic stirrer and deaerated by bubbling through a copious stream of nitrogen for 15 minutes. Then 10.97 g. (0.04 mole) of leuco-1,4,5,8-tetrahydroxyanthraquinone was added under nitrogen with stirring. The stirred mixture was chilled in an ice bath and 4.166 g. (0.04 mole) of 2-(2-aminoethylamino)ethanol was added dropwise via a hypodermic syringe through a rubber septum. The ice bath was removed. Stirring was continued for 2.5 hours as the temperature increased to about 22° C. The reaction mixture was gradually warmed with an oil bath which reached 50° C. over a 2 hour period, then 20.0 ml. of a 2 N solution of ammonia gas in 2-methoxyethanol was rapidly syringed into the flask. The reaction mixture was heated at 52° C. for 15 hours with stirring, then was allowed to cool. The mixture was chilled and 10.01 g. (0.04 mole) of chloranil was added followed by the dropwise addition of 10.0 ml. of 8 N ethanolic hydrogen chloride. The mixture was stirred for 15 hours without further cooling and the resultant solid was separated by centrifugation at 17,000 G to obtain a bulky pellet. This solid was washed by filtration with five 250 ml. portions of tetrahydrofuran to give 13.78 g. of a blue-purple-black solid.

A sample of the above material was analyzed by analytical high pressure liquid chromatography (HPLC) on a Partisil PxS 10/25 C8 column (Whatman, Inc.) using mobile phase A comprised of 77% water, 13% acetonitrile, 5% 2-methoxyethanol and 5% of 90% formic acid, with a flow rate of 1.5 ml/minute at 30° C. and detection by UV light at 254 nm. Successive components were eluted at 6.6 minutes (47.5%); 22.5 minutes (1.4%); 26.3 minutes (36.3%); and 39 minutes (14.9%). The component at 6.6 minutes was identified as 1,4-dihydroxy-5,8-bis[2-(2-hydroxyethylamino)ethylamino]anthraquinone dihydrochloride.

The above four components were then separated on a preparative scale by HPLC using the systems described below and about 0.2 g. of the crude product. The components eluted in the same order as above; the third component was the desired (title) compound. Thus a LOBAR Lichioprep ™ RP8 column (265 cm×31 cm, from E. Merck and Co.) was run at ambient temperature and a flow rate of one to 4 ml/minute, first using mobile phase B comprised of: 85% water, 5% acetonitrile, 5% 2-methoxyethanol and 5% of 90% formic acid (which rapidly eluted the first component), followed by mobile phase C, comprised of: 40% water, 25% acetonitrile, 25% 2-methoxyethanol and 10% of 90% formic acid. Fraction collection was monitored by UV at 254 nm as hereinabove described. Fractions containing the desired component were pooled and evaporated to dryness in vacuo. The resulting residue was then dissolved in mobile phase D, comprised of: 77% water, 13% acetonitrile, 5% 2-methoxyethanol and 5% of 90% formic acid, then rechromatographed on a Magnum 20 Partisil PxS 10μ C8 column (2 cm×25 cm, from Whatman, Inc.) at 30° C. and a flow rate of 8.0 ml/minute. The flow was monitored by UV at 254 nm to obtain the fraction containing the desired product. The fraction was evaporated in vacuo to give 28.0 mg. of the product of the product of the example. Chemical ionization mass spectroscopy and electron impact mass spectroscopy showed a molecular ion at M357 and (M+1) 357.9.

EXAMPLE 3

1-[2-(2-Hydroxyethylamino)ethylamino]-4-amino-5,8-dihydroxyanthraquinone monohydrochloride To a stirred solution of 35 g. (0.10 mole) of 2,3-dihydro-1,4,5,8-tetrahydroxy-9,10-anthracenedione (80% pure) in 750 ml. of methyl cellosolve in an inert, closed atmosphere at 10° C. was slowly added 25 ml. (0.10 mole) of a 4.0 M solution of 2-(2-aminoethylamino)ethanol in methyl cellosolve. The temperature was allowed to rise slowly to 20° C. The solution was then slowly heated to 50° C. and to it was slowly added 75 ml. (0.11 mole) of a 2.2 M solution of ammonia in methyl cellosolve. The mixture was then stirred at 50° C. in this sealed atmosphere for 20 hours. The crude "leuco" intermediate was then filtered as a brown powder. The brown powder was suspended in 500 ml. of methyl cellosolve and oxidized by adding 12 g. (0.10 mole) of chloranil followed by 200 ml. (0.50 mole) of 2.5 N ethanolic hydrogen chloride. The mixture was stirred at 25° C. overnight and was filtered to give 18 g. of blue-black powder. A 7.5 g. portion of this powder was dissolved in 50 ml. of hot water and filtered through a pad of acid-washed Celite. To the hot filtrate was added 50 ml. of ethanol and 50 ml. of tetrahydrofuran. The mixture was cooled and filtered to give 4.4 g. of the desired product as purple-black crystals, mp 276°–280° C.

I claim:

1. A compound selected from the group consisting of those of the formula:

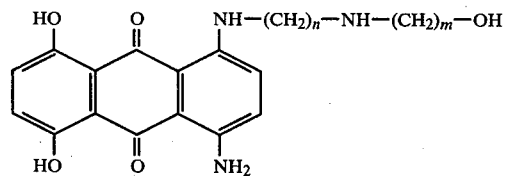

wherein n is an integer from 2 to 4, inclusive, and m is an integer from 2 to 4, inclusive; the leuco bases and tautomers thereof; and the pharmacologically acceptable acid-addition salts thereof.

2. The compound according to claim 1 wherein n is 2 and m is 2; 1-[2-(2-hydroxyethylamino)-ethylamino]-4-amino-5,8-dihydroxyanthraquinone.

3. The compound according to claim 1 wherein n is 2 and m is 2; leuco-1-[2-(2-hydroxythylamino)ethylamino]-4-amino-5,8-dihydroxyanthraquinone.

* * * * *